(12) United States Patent
Laroche et al.

(10) Patent No.: US 12,023,076 B2
(45) Date of Patent: Jul. 2, 2024

(54) OSTEOSYNTHESIS PLATE WITH AN ANCHORING ORIFICE INTENDED TO COOPERATE WITH AN OSTEOSYNTHESIS SCREW FOR COMPRESSION OF TWO BONE FRAGMENTS

(71) Applicant: NOVASTEP, Saint-Gregoire (FR)

(72) Inventors: Chloé Laroche, Rennes (FR); Loïc Girod, Goven (FR); Marc Augoyard, Tassin la Demi Lune (FR); Romain Augoyard, Tassin la Demi Lune (FR); Thimothée Bissuel, Lyons (FR); Tristan Meusnier, Saint Etienne (FR); Prikesht Mukish, Saint Genis Laval (FR); Stéphanie Valentin, Lyons (FR)

(73) Assignee: NOVASTEP, Saint-Gregoire (FR)

( * ) Notice: Subject to any disclaimer, the term of this patent is extended or adjusted under 35 U.S.C. 154(b) by 377 days.

(21) Appl. No.: 17/624,563

(22) PCT Filed: Jun. 30, 2020

(86) PCT No.: PCT/FR2020/051133
§ 371 (c)(1),
(2) Date: Jan. 3, 2022

(87) PCT Pub. No.: WO2021/005281
PCT Pub. Date: Jan. 14, 2021

(65) Prior Publication Data
US 2022/0249141 A1  Aug. 11, 2022

(30) Foreign Application Priority Data

Jul. 8, 2019 (FR) .................................. 19/07612

(51) Int. Cl.
*A61B 17/80* (2006.01)
*A61B 17/72* (2006.01)
*A61B 17/86* (2006.01)

(52) U.S. Cl.
CPC ...... *A61B 17/8014* (2013.01); *A61B 17/8057* (2013.01); *A61B 17/8605* (2013.01);
(Continued)

(58) Field of Classification Search
CPC ............ A61B 17/8014; A61B 17/8052; A61B 17/8605; A61B 17/8057; A61B 17/80;
(Continued)

(56) References Cited

U.S. PATENT DOCUMENTS

| 4,513,744 A | 4/1985 | Klaue |
| 2007/0233106 A1* | 10/2007 | Horan ................ A61B 17/8061 606/282 |

(Continued)

FOREIGN PATENT DOCUMENTS

| DE | 10 2006 000 948 A1 | 10/2006 |
| EP | 2 364 658 A1 | 9/2011 |

(Continued)

OTHER PUBLICATIONS

Oct. 15, 2020 Search Report issued in International Patent Application No. PCT/FR2020/051133.

*Primary Examiner* — Marcela I. Shirsat
(74) *Attorney, Agent, or Firm* — Oliff PLC

(57) ABSTRACT

An osteosynthesis plate includes a plate body in which there is formed an anchor through-orifice having a first orifice region and the second orifice region which are secant and joined by an intermediate region, the first orifice region being of plain cylindrical overall form and coinciding with a first virtual cylinder, the second orifice region having a second upper segment of plain spherical or frustoconical (Continued)

overall shape centred on a second axis and a second lower segment of threaded cylindrical overall shape and coinciding with a second virtual cylinder intersecting the first virtual cylinder, a helical rib being formed in the second orifice region to define a screw thread having a screw thread external radius smaller than the major radius of the second upper segment, and the intermediate region being formed of two planar intermediate faces facing one another.

8 Claims, 2 Drawing Sheets

(52) U.S. Cl.
CPC ......... *A61B 17/7225* (2013.01); *A61B 17/725* (2013.01); *A61B 17/8004* (2013.01); *A61B 17/8052* (2013.01); *A61B 17/8061* (2013.01)

(58) Field of Classification Search
CPC ............ A61B 17/8004; A61B 17/8061; A61B 17/808; A61B 17/84; A61B 17/86; A61B 17/861; A61B 17/8625; A61B 17/88; A61B 17/8841; A61B 17/7225; A61B 17/725
USPC .......... 606/282, 281, 280, 287, 291, 298, 71
See application file for complete search history.

(56) References Cited

U.S. PATENT DOCUMENTS

| | | | |
|---|---|---|---|
| 2009/0171399 A1* | 7/2009 | White | A61B 50/30 606/301 |
| 2012/0265255 A1* | 10/2012 | Hilse | A61B 17/8014 606/290 |
| 2018/0049788 A1* | 2/2018 | Rutledge | A61B 17/8042 |

FOREIGN PATENT DOCUMENTS

| | | |
|---|---|---|
| ES | 2223163 T3 | 2/2005 |
| ES | 2394257 T3 | 1/2013 |
| WO | 2007079814 A1 | 7/2007 |

* cited by examiner

[Fig. 1]
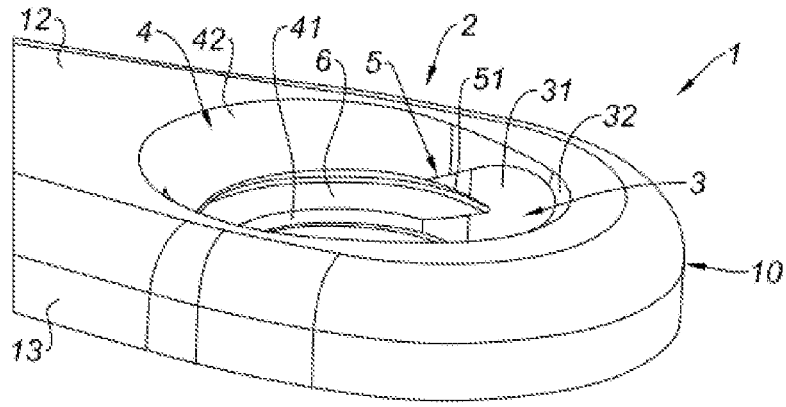
[Fig. 2]
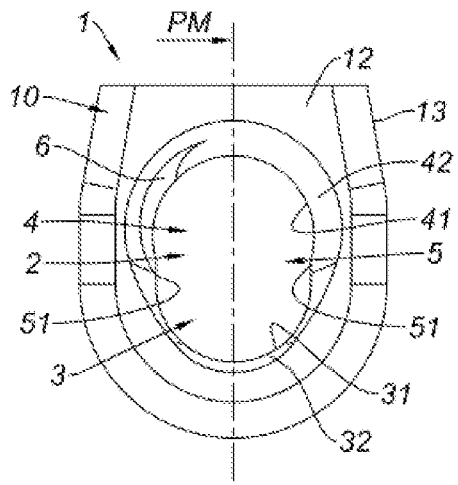
[Fig. 3]
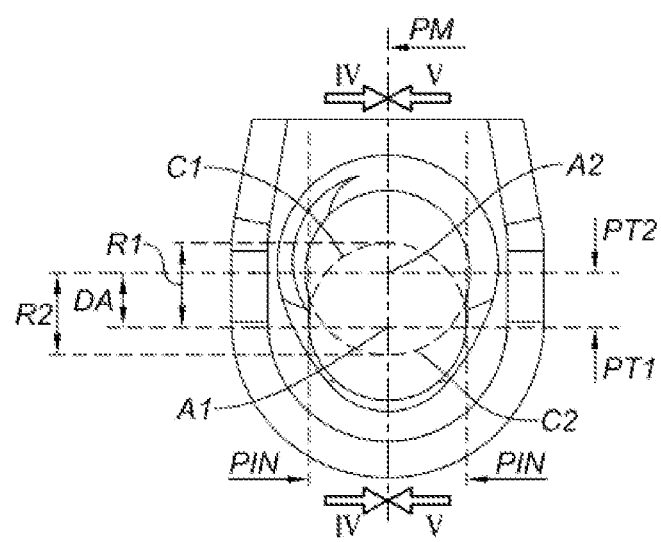

[Fig. 4]
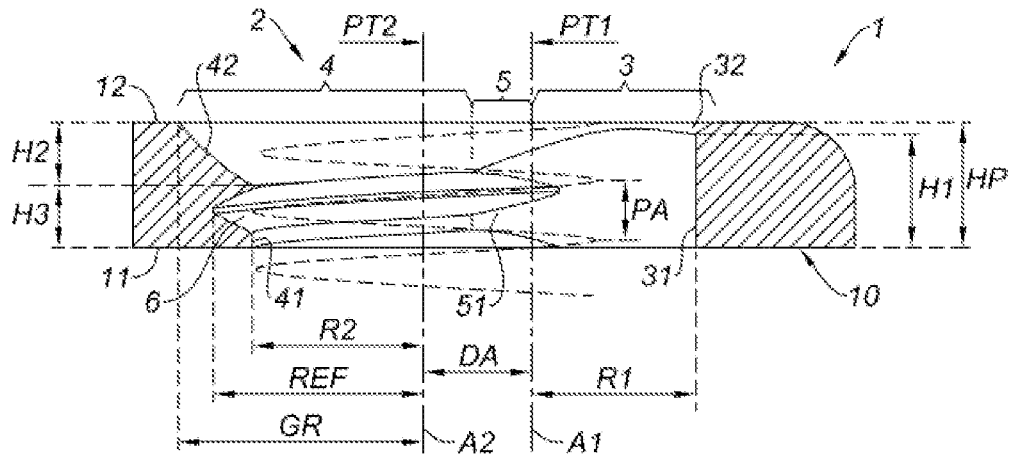
[Fig. 5]
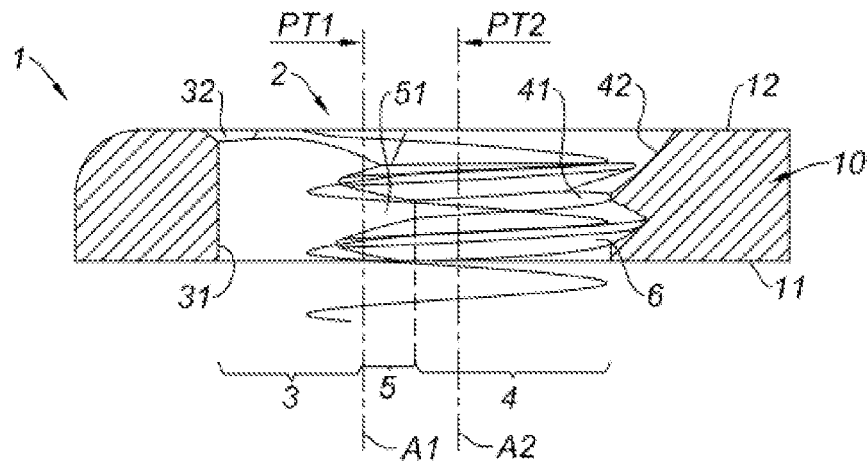
[Fig. 6]
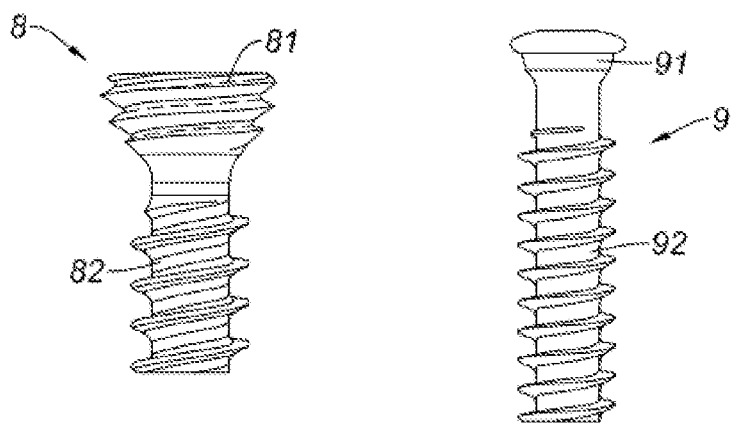

OSTEOSYNTHESIS PLATE WITH AN ANCHORING ORIFICE INTENDED TO COOPERATE WITH AN OSTEOSYNTHESIS SCREW FOR COMPRESSION OF TWO BONE FRAGMENTS

The invention relates to an osteosynthesis plate comprising a plate body having a lower face and an upper face, and in which is formed at least one anchoring orifice passing through the plate body by opening into the lower face and into the upper face, such an anchoring orifice being intended to cooperate with an osteosynthesis screw.

In the field of osteosynthesis plates, it is known to use anchoring orifices having a first smooth orifice region and a second partially threaded orifice region which are secant and joined by an intermediate region.

Thus, document EP2364658 proposes an anchoring orifice having a first orifice region successively having a spherical upper section and a cylindrical lower section, and a second orifice region successively having a threaded upper section and a frustoconical lower section.

A first drawback concerns the presence of a frustoconical lower section below the threaded upper section in the second orifice region, so that the thread does not extend over the entire height of the second orifice region, to the detriment of the retention of the osteosynthesis screw in this second orifice region.

A second drawback concerns the shape of the intermediate region which is in the form of two protruding ridges in the anchoring orifice, thus limiting the range of osteosynthesis screw diameter suitable for the anchoring orifice.

It is also known from the document DE 10 2006 000 948 A1 to provide an osteosynthesis plate provided with an anchoring orifice having a first orifice region successively having a frustoconical upper section and a cylindrical lower section, and a second orifice region having a threaded section over the entire height.

The invention aims at solving all or part of the aforementioned drawbacks, by providing an anchoring orifice the shape of which allows for an improved retention of the osteosynthesis screw, and this for several diameters of osteosynthesis screw.

To this end, the invention provides an osteosynthesis plate comprising a plate body having a lower face and an upper face, and wherein is formed at least one anchoring orifice passing through the plate body by opening into the lower face and into the upper face, said anchoring orifice having a main height defined between the lower face and the upper face and being intended to cooperate with an osteosynthesis screw for compression and stabilization of two bone fragments, said anchoring orifice having a first orifice region and a second orifice region which are secant and joined by an intermediate region; wherein the first orifice region has a first lower segment opening into the lower face and extending from the lower face over a first height at least equal to 90% of the main height, where this first lower segment has a smooth cylindrical general shape and coincides with a first virtual cylinder centered on a first axis orthogonal to the lower face and having a first predefined radius;

wherein the second orifice region is centered on a second axis parallel to the first axis and presents successively, starting from the upper face:
a second upper segment opening into the upper face and extending over a second height from the upper face, where the second upper segment has a smooth frustoconical or spherical general shape centered on the second axis and which has a decreasing radius from the upper face, starting from a large radius at the level of the upper face until reaching a small radius; and
a second lower segment prolonging the second upper segment, the second lower segment opening into the lower face and extending over a third height from the lower face, the second lower segment having a threaded cylindrical general shape and coincides with a second virtual cylinder centered on the second axis and having a second radius equivalent to the small radius of the second upper segment and larger than the first radius, said second virtual cylinder intersecting the first virtual cylinder;

wherein a helical rib is formed in the second upper segment and in the second lower segment to define a thread centered on the second axis, where said thread has a thread inner radius and a thread outer radius, said thread inner radius being equivalent to the second radius so that the helical rib extends into the second lower segment over the entire third height from the lower face, said thread outer radius being smaller than the large radius of the second upper segment so that the helical rib extends partly in the second upper segment without reaching the upper face; and wherein the intermediate region is formed of two planar intermediate faces extending opposite each other.

Thus, the invention proposes to have an anchoring orifice whose primary function, when in cooperation with an osteosynthesis screw, is, due to its shape, to make it possible to compress and stabilize two bone fragments and, if the osteosynthesis screw is a threaded-head screw, to also allow this compression to be locked.

This anchoring orifice has therefore secant first orifice region and second orifice region, with different radii (the second radius being larger than the first radius) and connected by planar intermediate faces. A helical rib is formed in the second orifice region to allow locking of an osteosynthesis threaded-head screw; the path of the rib following a helix to form a thread. This thread is produced so as to extend over almost the entire height of the second orifice region, which has the advantage of solidifying the retention between the osteosynthesis screw and the plate body by increasing the contact surface area between the thread of the screw head and that present in the second orifice region; it is noted that the second upper segment has a large radius larger than the outer radius of the thread so that this thread is not present over the entire second height of the second upper segment.

The first virtual cylinder and the second virtual cylinder are perpendicular to the lower face of the plate body, and the thread is also perpendicular to the lower face of the plate body because it is concentric around the second axis, so that an osteosynthesis screw can be locked by means of a cone/cylinder wedging between the screw head and the second upper segment respectively, and this has the advantage of simplifying the manufacture and dimensional control of a plate without compromising the screw/plate locking.

Finally, planar intermediate faces separate the first orifice region and the second orifice region, which has the advantage of being able to accept a wider range of osteosynthesis screw radius without compromising the screw/plate interface. Indeed, these planar intermediate faces make it possible to avoid the formation of sharp edges at the intersection of the two virtual cylinders, which offers a passage between the two orifice regions of increased width (compared to a theoretical case without these planar intermediate faces). This increase in the passage width between the orifice regions thus makes it possible to accept osteosynthesis screws whose diameters go up to this increased width, and this regardless of the positioning of the osteosynthesis screw, without interfering with sharp edges at the intersection of the two virtual cylinders.

In a particular embodiment, the planar intermediate faces extend in respective intermediate planes parallel to a midplane of the anchoring orifice, said midplane extending perpendicularly to the lower face with the first axis and the second axis included in said midplane.

According to one feature, the intermediate planes are tangent to the first virtual cylinder.

According to another feature, a first transverse plane extends orthogonally to the midplane passing through the first axis and a second transverse plane extends orthogonally to the midplane passing through the second axis, and the planar intermediate faces start from the first transverse plane without reaching the second transverse plane.

According to one possibility, the ratio between the second height and the third height is comprised between 0.8 and 1.25.

According to another possibility, the helical rib has a predefined pitch, and the ratio between the pitch and the third height is comprised between 0.8 and 1.25.

According to another possibility, the helical rib opens partially into at least one of the two planar intermediate faces.

In a particular embodiment, the first orifice region has a first upper segment forming a frustoconical chamfer opening into the upper face and prolonging the first lower segment.

Other features and advantages of the present invention will become apparent upon reading the detailed description below, of a non-limiting example of implementation, made with reference to the appended figures in which:

FIG. 1 is a partial schematic and perspective view of an osteosynthesis plate according to the invention, wherein an anchoring orifice is formed;

FIG. 2 is a schematic top view (upper face side) of the osteosynthesis plate in FIG. 1, FIG. 3 is a schematic top view (upper face side) of the osteosynthesis plate of FIG. 1, with illustrations of the virtual cylinders and of several planes;

FIG. 4 is a schematic sectional view of the osteosynthesis plate of FIG. 1, in the midplane of the anchoring orifice and according to the sectional plane IV-IV shown in FIG. 3;

FIG. 5 is a schematic sectional view of the osteosynthesis plate of FIG. 1, in the midplane of the anchoring orifice and according to the V-V sectional plane shown in FIG. 3;

FIG. 6 is a partial schematic view of two osteosynthesis screws adapted for an osteosynthesis plate according to the invention.

Referring to FIGS. 1 to 5, an osteosynthesis plate 1 according to an embodiment of the invention, comprises a plate body 10 having a lower face 11 and an upper face 12—the lower face 11 (visible only in FIGS. 4 and 5) forming the face capable of coming to bear against a bone—and a peripheral face 13 forming the periphery of the plate body 10 and joining the lower face 11 to the upper face 12. The lower face 11 and the upper face 12 are parallel to each other, at least at the level of the area where the anchoring orifice 2 described below is formed.

On this osteosynthesis plate 1, at least one anchoring orifice 2 is formed throughout the plate body 10 by opening into the lower face 11 and into the upper face 12. This anchoring orifice 2 having a main height HP defined between the lower face 11 and the upper face 12. This anchoring orifice 2 is intended to cooperate with an osteosynthesis screw 8, 9 for compression and stabilization of two bone fragments; such an osteosynthesis screw may be, with reference to FIG. 6, a threaded-head screw 8 comprising a threaded screw head 81 and a threaded screw body 82, or an unthreaded-head screw 9 comprising an unthreaded screw head 91 and a threaded screw body 92.

If the threaded-head screw 8 is used, the anchoring orifice 2 is intended to cooperate with this threaded-head screw 8 for compression and stabilization of two bone fragments, with locking of this compression by screwing the threaded screw head 81 into the thread of the second orifice region 4 (described below) of the anchoring orifice 2.

This anchoring orifice 2 is an oblong orifice, which is not axisymmetric, and which has a first orifice region 3 and a second orifice region 4 which are secant and joined by an intermediate region 5.

The first orifice region 3 presents successively starting from the lower face 11:
a first lower segment 31 opening into the lower face 11 and extending from the lower face 11 over a first height H1 at least equal to 90% of the main height HP, where this first lower segment 31 has a smooth cylindrical general shape and coincides with a first virtual cylinder C1 centered on a first axis A1 orthogonal to the lower face 11 and having a predefined first radius R1; and
a first upper segment 32 forming a frustoconical chamfer centered on the first axis A1 and opening into the upper face 12 and prolonging the first lower segment 31.

The second orifice region 4 is centered on a second axis A2 parallel to the first axis A1 and this second orifice region 4 has successively starting from the upper face 12:
a second upper segment 42 opening into the upper face 12 and extending over a second height H2 from the upper face 12, where the second upper segment 42 has a smooth frustoconical or spherical general shape centered on the second axis A2 and which has a decreasing radius from the upper face 12, starting from a large radius GR at the level of the upper face (12) until reaching a small radius R2 (also called second radius); and
a second lower segment 41 prolonging the second upper segment 42, the second lower segment 41 opening into the lower face 11 and extending over a third height H3 from the lower face 11, the second lower segment 41 having a threaded cylindrical general shape and coincides with a second virtual cylinder C2 centered on the second axis A2 and having a second radius R2.

This second radius R2 is equivalent to the small radius of the second upper segment 42 and furthermore this second radius R2 is larger than the first radius R1. As shown in FIG. 3, the second virtual cylinder C2 intersects the first virtual cylinder C1, in other words the inter-axis distance DA between the first axis A1 and the second axis A2 is smaller than the second radius R2 and also smaller than the first radius R1.

For the second lower segment 41 to be threaded, a helical rib 6 is formed in the second lower segment 41 and also in the second upper segment 42 and to define a thread centered on the second axis A2, where this thread has a thread inner radius and a thread outer radius REF.

The thread inner radius is equivalent to the second radius R2 so that the helical rib 6 extends into the second lower segment 41 over the entire third height H3 from the lower face 11.

The thread outer radius REF is smaller than the large radius GR of the second upper segment 42 so that the helical rib 6 extends partly into the second upper segment 42 without reaching the upper face 12, as shown in FIGS. 2 and 5.

In addition, the ratio between the second height H2 and the third height H3 is comprised between 0.8 and 1.25, in other words the second height H2 is substantially equivalent to the third height H3.

The helical rib 6 has a predefined pitch PA, and the ratio between the pitch PA and the third height H3 is comprised between 0.8 and 1.25, in other words the pitch PA is substantially equivalent to the third height H3.

The intermediate region 5 is formed of two planar intermediate faces 51 extending opposite each other and parallel to one another. More specifically, the two planar intermediate faces 51 extend in respective intermediate planes PIN parallel to a midplane PM of the anchoring orifice 2, where this midplane PM extends perpendicularly to the lower face 11 with the first axis A1 and the second axis A2 included in said midplane PM. Thus, these planar intermediate faces 51 extend symmetrically on either side of this midplane PM.

As shown in FIG. 3, these intermediate planes PIN are tangent to the first virtual cylinder C1.

As shown in FIGS. 3 to 5, a first transverse plane PT1 extends orthogonally to the midplane PM passing through the first axis A1 and a second transverse plane PT2 extends orthogonally to the midplane PM passing through the second axis A2, and the planar intermediate faces 51 start from the first transverse plane PT1 without reaching the second transverse plane PT2.

Moreover, and as shown in FIGS. 4 and 5, the helical rib 6 opens partially into the two planar intermediate faces 51.

When the anchoring orifice 2 cooperates with an osteosynthesis screw 8, 9, it makes it possible to compress two bone fragments thanks to a ramp formed by the second upper segment 42, and thanks to the second threaded lower segment 41; it is noted that this thread is perpendicular to the lower face 11 of the plate body 10 because it is concentric with the second axis A2, so that the locking of the osteosynthesis screw 8, 9 is achieved by means of a cone/cylinder wedging between respectively the screw head 81, 91 and the first orifice region 3. If the threaded-head screw 8 is used, this threaded-head screw 8 is blocked in the thread (formed of the helical rib 6), thus providing a locking of this compression.

The invention claimed is:

1. An osteosynthesis plate comprising a plate body having a lower face and an upper face, and wherein is formed at least one anchoring orifice passing through the plate body opening into the lower face and into the upper face, said anchoring orifice having a main height defined between the lower face and the upper face and being intended to cooperate with an osteosynthesis screw for a compression and a stabilization of two bone fragments, said anchoring orifice having a first orifice region and a second orifice region which are secant and joined by an intermediate region;

wherein the first orifice region has a first lower segment opening into the lower face and extending from the lower face over a first height at least equal to 90% of the main height, where this first lower segment has a smooth cylindrical general shape, and coincides with a first virtual cylinder centered on a first axis orthogonal to the lower face and having a predefined first radius;

wherein the second orifice region is centered on a second axis parallel to the first axis and has successively starting from the upper face:

a second upper segment opening into the upper face and extending over a second height from the upper face, where the second upper segment has a smooth frustoconical or spherical general shape centered on the second axis and which has a decreasing radius from the upper face, starting from a large radius at the level of the upper face until reaching a small radius; and a second lower segment prolonging the second upper segment, the second lower segment opening into the lower face and extending over a third height from the lower face, the second lower segment having a threaded cylindrical general shape and coincide with a second virtual cylinder centered on the second axis and having a second radius equivalent to the small radius of the second upper segment and larger than the first radius, said second virtual cylinder intersecting the first virtual cylinder;

wherein a helical rib is formed in the second upper segment and in the second lower segment to define a thread centered on the second axis, where said thread has a thread inner radius and a thread outer radius, said thread inner radius being equivalent to the second radius so that the helical rib extends into the second lower segment over the entire third height from the lower face, said thread outer radius being smaller than the large radius of the second upper segment so that the helical rib partly extends in the second upper segment without reaching the upper face; and wherein the intermediate region is formed of two planar intermediate faces extending opposite each other.

2. The osteosynthesis plate according to claim 1, wherein the planar intermediate faces extend in respective intermediate planes parallel to a midplane of the anchoring orifice, said midplane extending perpendicular to the lower face with the first axis and the second axis included in said midplane.

3. The osteosynthesis plate according to claim 2, wherein the intermediate planes are tangent to the first virtual cylinder.

4. The osteosynthesis plate according to claim 2, wherein a first transverse plane extends orthogonally to the midplane passing through the first axis and a second transverse plane extends orthogonally to the midplane passing through the second axis, and wherein the planar intermediate faces start from the first transverse plane without reaching the second transverse plane.

5. The osteosynthesis plate according to claim 1, wherein the ratio between the second height and the third height is comprised between 0.8 and 1.25.

6. The osteosynthesis plate according to claim 1, wherein the helical rib has a predefined pitch, and the ratio between the pitch and the third height is comprised between 0.8 and 1.25.

7. The osteosynthesis plate according to claim 1, wherein the helical rib opens partially into at least one of the two planar intermediate faces.

8. The osteosynthesis plate according to claim 1, wherein the first orifice region has a first upper segment forming a frustoconical chamfer opening into the upper face and prolonging the first lower segment.

* * * * *